(12) United States Patent
Brown

(10) Patent No.: US 6,599,897 B1
(45) Date of Patent: Jul. 29, 2003

(54) QUETIAPINE GRANULES

(75) Inventor: Daniel Boyd Brown, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/088,804

(22) PCT Filed: Sep. 18, 2000

(86) PCT No.: PCT/GB00/03598

§ 371 (c)(1),
(2), (4) Date: Mar. 21, 2002

(87) PCT Pub. No.: WO01/21179

PCT Pub. Date: Mar. 29, 2001

(30) Foreign Application Priority Data

Sep. 21, 1999 (GB) .............................. 9922271

(51) Int. Cl.$^7$ ...................... A61K 31/553; A61K 9/50
(52) U.S. Cl. .................................. 514/211.13; 424/499
(58) Field of Search ....................... 514/211.13; 424/499

(56) References Cited

U.S. PATENT DOCUMENTS 5,948,437 A    9/1999  Parikh et al.

FOREIGN PATENT DOCUMENTS

WO    WO 97/45124    12/1997

OTHER PUBLICATIONS

PCT/GB00/03598 International Search Report (Dec. 2000).

*Primary Examiner*—Raymond Henley, III
(74) *Attorney, Agent, or Firm*—George A. Gilbert

(57) ABSTRACT

Granule formulations of quetiapine and pharmaceutically acceptable salts thereof are described, as are their preparation and their use in treating diseases of the central nervous system such as psychotic disease conditions including schizophrenia.

38 Claims, No Drawings

QUETIAPINE GRANULES

This is a 371 of PCT/GB00/03598 filed Sep. 18, 2000.

The present invention relates to a novel pharmaceutical formulation comprising 11-[4-[2-(2-hydroxyethoxy)ethyl]-1-piperazinyl]dibenzo[b,f][1,4]thiazepine or a pharmaceutically acceptable salt thereof (hereinafter referred to as the "agent"), processes for its preparation, and its use. In particular the present invention relates to a formulation which is easily suspended or dissolved in aqueous media.

The "agent" can be used to treat diseases of the central nervous system such as psychoses. A particular example of the "agent" is quetiapine fumarate (sold under the trade name Seroquel®). Quetiapine fumarate has been marketed for a number of years for the treatment of schizophrenia and related disease conditions. A considerable body of literature describes how to use quetiapine fumarate. Specific references for the preparation and use of the "agent" are European Patent Application EP 240,228 and 282,236, U.S. Pat. No. 4,879,288 and International Patent Application WO 97/45124.

Quetiapine fumarate is marketed as a tablet. Although doctors, nurses and other carers try to ensure that the patient takes the tablet(s), in psychotic patients there is frequently a problem with non-compliance. For example, the patient may "cheek" the tablet resulting in a missed dosage. Compliance problems would be reduced if the "agent" could be administered in the form of an oral solution or suspension. An oral solution or suspension has the additional advantage of being easier to swallow and hence a better method of administration for those patients who have problems swallowing tablets.

To avoid problems with the "agent" deteriorating, the formulation of the present invention is provided as low moisture content granules which are readily dissolved or suspended in aqueous media prior to administration. The granules are also free flowing which enables uniform filling and emptying of sachets so that an accurate dose of the therapeutic product can be administered.

Various low moisture content formulations of the "agent" were prepared but found to be unsuitable, because either the granules were too hard and therefore not easily dispersed, or were not free flowing and compacted upon standing or vibration.

Eventually we found a granule formulation of the "agent" which was free flowing and yet also surprisingly easily dissolved or suspended in aqueous media. Thus, the present invention provides a granule formulation of the "agent" which is free flowing and easily dissolved or suspended in aqueous media. For example, it should be suitable for administration within the time scale of the person administering the dose. Typically, it should be suitable for administration in less than 15 minutes, preferably less than 5 minutes and more preferably in less than 2 minutes.

In particular, the present invention provides a granule formulation comprising 11-[4-[2-(2-hydroxyethoxy)ethyl]-1-piperazinyl]dibenzo[b,f][1,4]thiazepine or a pharmaceutically acceptable salt thereof and a freely or very water-soluble binder, wherein the granules have a bulk density range of 0.15 g/ml to 0.60 g/ml and a tap density range of 0.20 g/ml to 0.70 g/ml and 80% of the granules are in the size range of 75 to 850 microns.

The preparation, physical properties and beneficial pharmacological properties of the "agent" are described in published European Patents EP 240,228 and 282,236 as well as in U.S. Pat. No. 4,879,288, the entire contents of which are herein incorporated by reference.

Preferably the "agent" is 11-[4-[2-(2-hydroxyethoxy)ethyl]-1-piperazinyl]dibenzo[b,f][1,4]thiazepine or a highly water-soluble pharmaceutically acceptable salt thereof. More preferably the "agent" is 11-[4-[2-(2-hydroxyethoxy)ethyl]-1-piperazinyl]dibenzo[b,f][1,4]thiazepine or a dihydrochloride, maleate, citrate or a fumarate salt thereof. Most preferably the "agent" is quetiapine fumarate (Seroquel).

A freely or very water-soluble binder is a binder which dissolves in less than 10 parts of water per 1 part of binder by weight and comprises maltodextrin, mannitol, xylitol, pre-gelatin starch, sucrose or poly[1-(2-oxo-1-pyrrolidinyl)ethylene] (povidone). Preferably the binder dissolves in less than 1 part of water per 1 part of binder.

Preferably the very water-soluble binder is maltodextrin.

Preferably, the present invention provides a granule formulation comprising Seroquel® and maltodextrin, wherein the granules have a bulk density range of 0.15 g/cc to 0.60 g/cc and a tap density range of 0.20 g/cc to 0.7 g/cc and 80% of the granules are in the size range of 75 to 850 microns.

Bulk density is the density of a free flowing powder. Tap density is the density of the powder after it has been vibrated or tapped on a surface several times. Bulk density is determined by pouring a volume of 100 ml of powder into a graduated cylinder and measuring the weight of the powder. Tap density is determined by placing the same cylinder, containing the 100 ml of powder used to measure the bulk density, on a piece of equipment that raises and drops the cylinder 200 times (the amplitude of the raising and lowering in this standard test is 0.5 inches). The new volume of the powder is measured and since the weight of the powder is already known the tap density can be calculated.

Preferably the granules have a bulk density range of 0.261 g/ml to 0.400 g/ml; in particular 0.261 g/ml to 0.368 g/ml.

Preferably the granules have a tap density range of 0.342 g/ml to 0.500 g/ml; in particular 0.342 g/ml to 0.464 g/ml.

Granules with the desired bulk density, tap density and size range characteristics can be formed by using a fluid bed process. The fluid bed process involves fluidising the components of the formulation on a bed of air, adding water and then drying. Components of the formulation could alternatively be added as a solution or suspension with the water.

Accordingly, in another aspect, the present invention provides a process for preparing a formulation as defined above which comprises:

i) fluidising one or more components on a bed of air in a fluid bed;

ii) adding, to the fluid bed, water optionally containing one or more components;

iii) drying.

Preferably the "agent" and the freely or very water-soluble binder and any other components are fluidised on the bed of air.

The fluid bed process is well known in the art, for example see Schaefer T., Worts O., Control of Fluidized Bed Granulation I. Effect of spray angle, nozzle height and starting materials on granule size and size distribution, Arch. Pharm. Chemi Sci. Ed. 5, 1977, 51–60; Schaefer T., Worts O., Control of Fluidized Bed Granulation II. Estimation of Droplet Size of Atomized Binder Solutions, Arch. Pharm. Chemi Sci. Ed. 5, 1977, 178–193; Schaefer T., Worts O., Control of Fluidized Bed Granulation III. Effects of Inlet Air Temperature and Liquid Flow Rate on Granule Size and Size Distribution. Control of Moisture Content on Granules in the Drying Phase, Arch. Pharm. Chemi Sci. Ed. 6, 1978, 1–13;

Schaefer T., Worts O., Control of Fluidized Bed Granulation IV. Effects of Binder Solution and Atomization on Granule size and size distribution, Arch. Pharm. Chemi Sci. Ed. 6, 1978, 14–25; Schaefer T., Worts O., Control of Fluidized Bed Granulation V. Factors Affecting Granule Growth, Arch. Pharm. Chemi Sci. Ed. 6, 1978, 69–82; Kawai S., Granulation and Drying of Powdery or Liquid Materials by Fluidized Bed Technology, Drying technology, 11(4), 1993, 719–731; and Kokubo H., Sunada H., Effect of Process Variable on the Properties and Binder Distribution of Granules Prepared in a Fluidized Bed, Chem. Pharm. Bull. 45(6), 1997, 1069–1072.

The size and density of the granules can be affected by altering conditions such as temperature, atomnisation air pressure, process air volume and water addition spray rate used in the fluid bed process. A key parameter affecting the characteristics of the granules is the moisture level in the granules; this moisture level results from the moisture level that is built up in the fluid bed. Granules with the desired characteristics can be obtained by altering the moisture level built up in the fluid bed using standard methods known in the art until granules of the appropriate size range and density are obtained. For example, on a 15 kg scale, the moisture level in the granules is normally between 4 and 10%. Typical conditions on the 15 kg scale are an inlet air temperature of 55–70° C., an atomisation air pressure of 0.5 to 3.5 bar, a process air volume of 150 to 225 cfm (cubic foot per minute) and a water addition spray rate of 100 to 150 ml/min. Granules with the desired physical characteristics could also be formed using conditions outside these ranges. For example, on a larger scale (225 Kg), granules according to the invention were prepared using an inlet air temperature of 55–80° C., an atomisation air pressure of 1.0 to 3.0 bar, a process air volume of 1600 to 2200 cfm and a water addition spray rate of 600 to 900 ml/min.

In a preferred aspect, the present invention provides a fluid bed process wherein the moisture content is controlled to give granules with a moisture level in the range of 1.5 to 15%.

In another aspect, the present invention provides granules with a moisture level in the range of 1.5 to 15% preferably 3 to 10%, more preferably 4 to 8%.

Preferably the moisture level in the fluid bed leads to granules having a moisture level in the range 3 to 10%. More preferably the moisture level in the fluid bed leads to granules having a moisture level in the range 4 to 8%.

In a preferred aspect, the present invention provides a fluid bed process wherein the atomisation air pressure is in the range of 0.5 to 3.5 bar, for example 1.0 to 3.0 bar.

In a further aspect, the present invention provides a granule formulation comprising the "agent" and a freely or very water-soluble binder produced by a fluid bed process wherein the moisture level in the granules before drying is in the range 1.5 to 15%.

In a preferred aspect, the present invention provides a granule formulation comprising the "agent" and a freely or very water-soluble binder produced by a fluid bed process wherein the atomisation air pressure is in the range of 0.5 to 3.5 bar, for example 1.0 to 3.0 bar.

In a further aspect, the present invention provides a granule formulation comprising the "agent" and a freely or very water-soluble binder, wherein the granules have a bulk density range of 0.15 g/ml to 0.60 g/ml and a tap density range of 0.20 g/ml to 0.70 g/ml and 80% of the granules are in the size range of 75 to 850 microns; produced by a fluid bed process.

Preferably, the present invention provides a granule formulation comprising Seroquel® and maltodextrin, wherein the granules have a bulk density range of 0.15 g/ml to 0.60 g/ml and a tap density range of 0.20 g/ml to 0.70 g/ml and 80% of the granules are in the size range of 75 to 850 microns, produced by a fluid bed process.

Preferably the formulation contains a sweetener or sweeteners to enhance its taste. Suitable sweeteners include aspartame, MagnaSweet®, sucrose, saccharin, sodium cyclamate and acesultame potassium. Preferred sweeteners are aspartame and MagnaSweet®.

Other excipients such as suspending agents that are compatible with the "agent" could be added to the formulation to increase the length of time that the formulation remains as a suspension in the aqueous media. Examples of suspending agents include sodium starch glycolate, starch, guar gum and povidone. However, we have found that the formulation dissolves or remains remarkably well suspended without the need for suspending or thickening agents and this forms another aspect of the invention. For example, the 25 mg granule formulation described in the Examples below surprisingly forms a solution in 30 ml of water in approximately 15–20 seconds. The 150 mg granule formulation described in the Examples below forms a suspension in 30 ml of water in approximately 10 seconds with gentle stirring and remains as a suspension for about 10 minutes. It can easily be re-suspended with gentle swirling in a matter of seconds.

Surprisingly, not only is a suspending agent generally not needed, but also we have discovered that the typical suspending agent, xanthan gum, is generally not suitable as suspending agent in the formulations of the present invention.

Preferably the formulation does not include a suspending agent.

Likewise surfactants that are compatible with the "agent", such as polysorbates, glyceryl monooleate and sorbitan esters, can be added to the formulation, but we have found that the granule formulation performs well without the need for them.

Preferably the formulation does not include a surfactant.

Preferably, the present invention provides a granule formulation consisting of 11-[4-[2-(2-hydroxyethoxy)ethyl]-1-piperazinyl]dibenzo[b,f][1,4]thiazepine or a pharmaceutically acceptable salt thereof, a freely or very water-soluble binder and a sweetener, wherein the granules have a bulk density range of 0.15 g/ml to 0.60 g/ml and a tap density range of 0.20 g/ml to 0.70 g/ml and 80% of the granules are in the size range of 75 to 850 microns. In a preferred aspect 11-[4-[2-(2-hydroxyethoxy)ethyl]-1-piperazinyl]dibenzo[b,f][1,4]thiazepine is in the form of a fumarate salt.

The granules of the present invention are readily dissolved or suspended in aqueous media. The aqueous media is not necessary water, but includes substances with a sufficient water content, for example fruit/vegetable juices, sauces or purees such as desserts.

Preferably the pH of resulting solution/suspension is between pH4 and pH9. More preferably, the pH of resulting solution/suspension is between pH5 and pH6.

In another aspect the invention relates to a granule formulation as defined above either dissolved or suspended in aqueous media.

The dose of the compound of the present invention which is administered will necessarily be varied according to principles well known in the art taking account of the route of administration, the duration of treatment, the severity of the psychotic condition, the size and age of the patient, the potency of the active component and the patient's response thereto. An effective dosage amount of the active component can thus readily be determined by the clinician after a consideration of all criteria and using his best judgement on the patient's behalf. In general, the compound will be administered to a warm blooded animal (such as man) so that an effective dose is received, generally a daily dose in the range of about 0.01 to about 40 mg/kg body weight. For example, when administered orally, it is generally administered in the range of about 0.1 to about 40 mg/kg body weight.

Preferably, the compound of the present invention is administered in about a 25, 50, 100, 125 or 150 mg strength.

It will be apparent to those skilled in the art that the formulation can be co-administered with other therapeutic or prophylactic agents and/or medicaments that are not medically incompatible therewith. The compound of the present invention does not, in general, show any indication of overt toxicity in laboratory test animals at several multiples of the minimum effective dose of the active ingredient.

According to another aspect of the invention there is provided a granule formulation as defined above, for use as a medicament.

According to another aspect of the present invention there is provided a method of treating psychosis, especially schizophrenia, by administering an effective amount of a granule formulation as defined above, to a mammal in need of such treatment.

The invention is further illustrated by the following non-limiting Examples in which temperatures are expressed in degrees Celsius. The "agent" may be prepared as described in published European Patents EP 240,228 or 282,236 as well as in U.S. Pat. No. 4,879,288.

EXAMPLES

Example 1

Two different strength formulations were prepared. The first contained 25 mg of quetiapine free base (the 25 mg formulation) and the second 150 mg of quetiapine free base (the 150 mg formulation).

The composition of formulations is shown below:

| Ingredient | 25 mg (mg/dose) | 150 mg (mg/dose) |
|---|---|---|
| Quetiapine fumarate | 28.8 | 172.7 |
| Maltodextrin, NF | 950.0 | 767.3 |
| Aspartame, NF | 21.2 | 30.0 |
| MagnaSweet 135 ® | | 30.0 |
| Purified Water, USP | q.s. (~186.0) | q.s. (~186.0) |

Quetiapine fumarate is equivalent to 86.8% quetiapine free base. Purified water was sprayed in a sufficient amount and manner to provide granules with a moisture content of 5.6%.

Maltodextrin may be purchased as Maltrin M-100 from, for example, Grain Processing Corporation. MagnaSweet 135® may be purchased from MAFCO Worldwide Corporation.

The formulations were prepared using fluid bed technology. A Glatt GPCG-60 fluid bed processor is used on the 15 kg and 50 kg scale. A Glatt GPCG-300 fluid bed processor is used on the 225 kg scale. The fluid bed processor was configured for top spray fluid bed granulation and as shown below:

| Apparatus | Glatt GPCG-60 | Glatt GPCG-300 |
|---|---|---|
| Water Pump | Peristaltic | Peristaltic |
| Inlet Air Dew Point | 10° C. | 10° C. |
| Port Size | 1.2 mm | 1.5 m |
| Number of Ports in Nozzle Head | 3 | 6 |
| Nozzle Height | #4 | #4 |
| Bottom Screen | 100 mesh | 100 mesh |
| Shake Mode | GPCG | GPCG |
| Shake Interval | 30 sec | 60 sec |
| Shake Duration | 3 sec | 5 sec |

The following processing conditions were used:

| | | Glatt GPCG-60 Processing Parameters | | | |
|---|---|---|---|---|---|
| Batch | Strength | Inlet Temp (° C.) | Process Air Volume (cfm) | Atomisation Air Pressure (bar) | Pump Rate (g/min) Water Addition Spray Rate |
| a | 25 mg | 65 | 850 | 2.0 | 360 |
| b | 150 mg | 65 | 850 | 2.0 | 360 |
| c | 150 mg | 65 | 850 | 1.7 | 360 |
| d | 150 mg | 65 | 850–750 | 1.5 | 360 |

| | | Glatt GPCG-300 Processing Parameters | | | |
|---|---|---|---|---|---|
| Batch | Strength | Inlet Temp (° C.) | Process Air Volume (cfm) | Atomisation Air Pressure (bar) | Pump Rate (g/min) Water Addition Spray Rate |
| a | 25 mg | ~70 | 1850 | 2.0 | 800 |
| b | 25 mg | ~70 | 1850 | 2.0 | 800 |
| c | 150 mg | ~70 | 1800 | 1.5 | 800 |
| d | 150 mg | ~70 | 1800 | 1.5 | 800 |

All of the ingredients were added to the fluid bed granulator bowl. The material was then fluidized. After approximately 2 to 3 minutes, water (186 ml per 1 gram of components) was sprayed into the expansion chamber. The total processing time for each batch was less than one hour.

Results from the GPCG-60 (50 kg Scale)

| Batch | Sieve Analysis Data[1] -% Retained (μm) | | | | | | | Density (g/ml) | | Moisture[2] - % | |
|---|---|---|---|---|---|---|---|---|---|---|---|
| | 850 | 425 | 250 | 180 | 150 | 75 | Pan | Bulk | Tap | EOS[3] | Final[4] |
| a | 0.4 | 4.8 | 19.8 | 21.8 | 11.1 | 31.6 | 10.5 | 0.29 | 0.39 | 9.3 | 5.4 |
| b | 0.3 | 22.0 | 13.7 | 20.0 | 11.7 | 38.9 | 13.2 | 0.36 | 0.35 | 7.9 | 3.8 |
| c | 0.2 | 3.3 | 18.2 | 21.9 | 10.8 | 33.1 | 12.5 | 0.34 | 0.41 | 7.4 | 4.3 |
| d | 1.6 | 12.2 | 28.9 | 20.0 | 7.7 | 19.1 | 10.5 | 0.31 | 0.42 | 8.7 | 5.9 |

Results from the GPCG-300 (225 kg Scale)

| Batch | Sieve Analysis Data[1] -% Retained (mesh) (μm) | | | | | | | Density (g/ml) | | Moisture[2] - % | |
|---|---|---|---|---|---|---|---|---|---|---|---|
| | 850 | 425 | 250 | 180 | 150 | 75 | Pan | Bulk | Tap | EOS[3] | Final[4] |
| a | 2.8 | 13.1 | 33.4 | 23.8 | 10.1 | 13.0 | 3.8 | 0.26 | 0.35 | 6.2 | 6.0 |
| b | 1.7 | 12.2 | 32.9 | 25.3 | 9.9 | 15.7 | 2.3 | 0.26 | 0.28 | 7.5 | 6.7 |
| c | 2.5 | 17.6 | 33.6 | 19.5 | 9.5 | 11.3 | 6.0 | 0.36 | 0.42 | 6.7 | 5.3 |
| d | 5.8 | 23.9 | 32.7 | 17.2 | 8.3 | 8.0 | 4.1 | 0.29 | 0.37 | 7.4 | 6.6 |

[1]Data generated using 100 gram sample processed for 5 minutes on Tyler sieve shaking apparatus.
[2]Moisture was determined at using a Computrac Moisture Balance set 105° C.
[3]End of Spray.
[4]Moisture level of granules after drying.

Example 2

The formulations from Example 1 above are filled into sachets in a conventional manner.

What is claimed is:

1. A granule formulation comprising 11-[4-[2-(2-hydroxyethoxy)ethyl]-1-piperazinyl]dibenzo[b,f][1,4]thiazepine or a pharmaceutically acceptable salt thereof and a freely or very water-soluble binder, wherein the granules have a bulk density range of 0.15 g/cc to 0.60 g/cc and a tap density range of 0.20 g/cc to 0.70 g/cc and 80% of the granules are in the size range of 75 to 850 microns.

2. A formulation according to claim 1 wherein 11-[4-[2-(2-hydroxyethoxy)ethyl]-1-piperazinyl]dibenzo[b,f][1,4]thiazepine is in the form of a fumarate salt.

3. A formulation according to either claim 1 or claim 2 wherein the freely or very water-soluble binder comprises maltodextrin, mannitol, xylitol, pre-gelatinised starch, sucrose or poly[1-(2-oxo-1-pyrrolidinyl)ethylene].

4. A formulation according to claim 3 wherein the binder is maltodextrin.

5. A formulation according claim 1 wherein the bulk density range is 0.26 g/cc to 0.400 g/cc d the tap density range is 0.342 g/cc to 0.500 g/cc.

6. A formulation according to claim 1 which further comprises a sweetener.

7. A granule formulation consisting of 11-[4-[2-(2-hydroxyethoxy)ethyl-1-piperazinyl]dibenzol[b,f][1,4]thiazepine or a pharmaceutically acceptable salt thereof, a freely or very water-soluble binder, and a sweetener wherein the granules have a bulk density range of 0.15 g/cc to 0.60 glcc and a tap density range of 0.20 g/cc to 0.70 g/cc and 80% of the granules are in the size range of 75 to 850 microns.

8. A formulation according to claim 7 wherein 11-[4-[2-(2-hydroxyethoxy)ethyl-1-piperazinyl]dibenzol[b,f][1,4]thiazepine is in the form of a fumarate salt.

9. A formulation according to claim 1 wherein the moisture level in the granules is between 1.5 and 15%.

10. A formulation according to claim 9 wherein the moisture level in the granules is between 4 and 8%.

11. A process for preparing a formulation as defined in claim 1 which process comprises:
(i) fluidizing 11-[4,2-(2-hydroxyethoxy)ehtyl-1-piperazinyl]dibenzo[b,f][1,4]thiazepine or a pharmaceutically acceptable salt thereof and the freely or very water-soluble binder on a bed of air in a fluid bed;
(ii) adding water to the fluid bed; and
(iii) drying.

12. A method for treating pschosis which comprises administering an effective amount of a formulation as defined in claim 1 to a patient in need thereof.

13. A kit comprising
i) a granule formulation as defined in claim 1;
ii) an aqueous medium;
iii) optionally, instructions for use so that the granules can be dissolved or suspended in said aqueous medium for administration.

14. A formulation according to claim 2 wherein the bulk density range is 0.26 g/cc to 0.400 g/cc d the tap density range is 0.342 g/cc to 0.500 g/cc.

15. A formulation according to claim 3 wherein the bulk density range is 0.26 g/cc to 0.400 g/cc d the tap density range is 0.342 g/cc to 0.500 g/cc.

16. A formulation according to claim 4 wherein the bulk density range is 0.26 g/cc to 0.400 g/cc d the tap density range is 0.342 g/cc to 0.500 g/cc.

17. A formulation according to claim 2 which further comprises a sweetener.

18. A formulation according to claim 3 which further comprises a sweetener.

19. A formulation according to claim 4 which further comprises a sweetener.

20. A formulation according to claim 5 which further comprises a sweetener.

21. A formulation according to claim 1 wherein the moisture level in the granules is between 1.5 and 15%.

22. A formulation according to claim 2 wherein the moisture level in the granules is between 1.5 and 15%.

23. A formulation according to claim 3 wherein the moisture level in the granules is between 1.5 and 15%.

24. A formulation according to claim 4 wherein the moisture level in the granules is between 1.5 and 15%.

25. A formulation according to claim 5 wherein the moisture level in the granules is between 1.5 and 15%.

26. A formulation according to claim 6 wherein the moisture level in the granules is between 1.5 and 15%.

27. A formulation according to claim 7 wherein the moisture level in the granules is between 1.5 and 15%.

28. A formulation according to claim 8 wherein the moisture level in the granules is between 1.5 and 15%.

29. A formulation according to claim 2 wherein the moisture level in the granules is between 4% and 5%.

30. A formulation according to claim 3 wherein the moisture level in the granules is between 4 and 8%.

31. A formulation according to claim 4 wherein the moisture level in the granules is between 4 and 8%.

32. A formulation according to claim 5 wherein the moisture level in the granules is between 4 and 8%.

33. A formulation according to claim 6 wherein the moisture level in the granules is between 4 and 8%.

34. A formulation according to claim 7 wherein the moisture level in the granules is between 4 and 8%.

35. A formulation according to claim 8 wherein the moisture level in the granules is between 4 and 8%.

36. The method as recited in claim 12 wherein the disease of the central nervous system is psychoses.

37. The method as recited in claim 36 where the disease of the central nervous system is schizophrenia.

38. The method according to claim 12 wherein the psychosis is schizophrenia.

* * * * *